(12) United States Patent
Bancroft (10) Patent No.: US 8,465,695 B2
(45) Date of Patent: Jun. 18, 2013

(54) WASHING TEST APPARATUS (75) Inventor: Richard Bancroft, Leicester (GB)

(73) Assignee: Albert Browne Limited, Leicester (GB)

( * ) Notice: Subject to any disclaimer, the term of this patent is extended or adjusted under 35 U.S.C. 154(b) by 868 days.

(21) Appl. No.: 10/555,502

(22) PCT Filed: Apr. 30, 2004

(86) PCT No.: PCT/GB2004/001875
§ 371 (c)(1),
(2), (4) Date: Sep. 6, 2006

(87) PCT Pub. No.: WO2004/098429
PCT Pub. Date: Nov. 18, 2004

(65) Prior Publication Data
US 2007/0053791 A1 Mar. 8, 2007

(30) Foreign Application Priority Data
May 3, 2003 (GB) .................................. 0310280.3

(51) Int. Cl.
*G01N 33/00* (2006.01)
(52) U.S. Cl.
USPC .............. 422/68.1; 422/69; 422/70; 422/560; 422/561

(58) Field of Classification Search
USPC ................ 422/58, 68.1, 99, 102, 69, 70, 560, 422/561
See application file for complete search history.

(56) References Cited

U.S. PATENT DOCUMENTS

| | | | | |
|---|---|---|---|---|
| 2,891,814 A | * | 6/1959 | Idoine et al. | 294/99.2 |
| 4,643,980 A | * | 2/1987 | Witonsky et al. | 436/128 |
| 5,172,837 A | * | 12/1992 | Finney et al. | 223/23 |
| 5,674,395 A | * | 10/1997 | Stankowski et al. | 210/321.75 |
| 6,742,683 B1 | * | 6/2004 | Phan | 223/84 |
| 2001/0033805 A1 | | 10/2001 | Jacobs et al. | |

FOREIGN PATENT DOCUMENTS

| | | |
|---|---|---|
| DE | 4437103 A | 4/1996 |
| DE | 29909783 U | 12/1999 |
| DE | 19962148 A | 7/2001 |
| DE | 20108346 U | 9/2001 |
| EP | 0557701 A | 9/1993 |

* cited by examiner

Primary Examiner — Sam P Siefke
(74) Attorney, Agent, or Firm — LeClairRyan, a Professional Corporation (57) ABSTRACT

Washing efficacy test apparatus (2) is provided which includes a holder (4) and a test soil device (6) for location with said holder (4). The test soil device (6) is in the form of sheet material with a test soil substance (34) provided thereon. The holder in one example includes two members (8, 10) between which the test soil device (6) is detachably attached so that the device (6) can be easily removed for inspection and maintained in a required orientation in the washing apparatus (2) in use.

21 Claims, 13 Drawing Sheets

INDEX

1. Clip face down
2. Clip on side
3. Clip on side
3. Test strip placed flat on shelf
3. Clip face down
3. Clip on side 7. Test strip looped through shelf
8. Test strip placed flat on shelf
9. Test strip placed flat on shelf
10. Test strip looped through shelf
11. Test strip placed flat on shelf
12. Test strip looped through shelf

WASHING TEST APPARATUS

This application is a national stage application under 35 U.S.C. §371 from PCT Application No. PCT/GB2004/001875, filed Apr. 30, 2004, which claims the priority benefit of Great Britain Application No. 0310280.3, filed May 3, 2003.

This invention relates to washing/cleaning efficacy test apparatus, and particularly but not necessarily exclusively to washing/cleaning efficacy test apparatus for clinical and/or laboratory use.

Surgical instruments and other medical devices used for clinical or laboratory purposes must be reprocessed or decontaminated after use, if they are non-disposable, in order to prevent infection and cross contamination. The decontamination process typically involves 3 steps; a washing/cleaning step to remove blood, proteins and other bodily contaminants from the instruments and/or devices, followed by a disinfection step to allow safe handling and inspection of the devices/instruments prior to packaging, and the final step of sterilisation. If the devices/instruments are sterilised without effective washing/cleaning or disinfection, sterilisation is likely to be ineffective.

The cleaning/washing and disinfection steps are two distinct stages in the decontamination process but are often undertaken in the same washing apparatus (a washer disinfector) in a sequential manner using different programmable cycles. The efficacy of the disinfection step (a heat process) can be verified thermometrically but the efficacy of the washing/cleaning step cannot be easily measured parametrically. As such, a test substance known as a "test soil" is used as a challenge in the washing apparatus and includes a pre-determined level of contaminants thereon, which is designed to simulate typical soiling of surgical instruments and medical devices during normal use. The "test soil" is coated onto a selection of surgical instruments and/or medical devices and is allowed to dry onto to the same for a period of time. The instruments and/or devices are then processed through the washing apparatus or washer disinfector to test the efficacy of the washing/cleaning step. Removal of "test soil" from the instruments and devices can be determined visually since most test soils contain blood or dyes to make them visible. Alternatively, a chemical detection method such as ninhydrin (1,2,3-indantrione monohydrate) can be used. The ninhydrin method utilises the reaction of amino acids, peptides and proteins with the ninhydrin to produce a highly coloured compound. A selection of instruments are swabbed with water, then the swab is treated with ninhydrin. IF protein is present on the instruments, i.e. if the instruments are not clean, the swab turns a purple colour.

Conventional test soils typically include animal blood or blood fractions and other animal products, such as egg or egg fractions. However, the natural variability of the test soil components can mean that the test soils may not perform consistently from batch to batch. In addition, the test soils need to be coated onto a range of instruments and allowed to dry for between 30 minutes to two hours prior to washing. This is time consuming and is typically a major inconvenience for busy hospital departments. There are also problems associated with the availability of fresh test soil components and, due to the problems mentioned above, the test is normally conducted on a periodic basis which, in some cases, is as infrequently as four times a year. As such, any problems which might arise with the washing process are only identified infrequently. Furthermore, due to the well known risks associated with using blood products, it is undesirable to use the same in the manner described above.

An example of a conventional test soil device which is used in the monitoring of the cleaning efficiency of washer disinfection apparatus includes a standardised test soil substance which is placed at an amount of 20 mg on a small stainless steel plate. The test soil consists of 95% water soluble components and 5% water insoluble fibrin fibres which correlates to coagulated human blood.

A problem associated with such a conventional test device is that it is generally unidirectional and is exposed to washing and cleaning in one direction only. However, since the efficacy of the washing and cleaning processes is dependent on factors such as the operating cycle being used, temperature and pressure of the water, the location of the test device in the washing apparatus, loading of the washing apparatus and whether the test device is adjacent water/fluid jets in the washing apparatus, if only a single surface of the test device has a test soil substance provided thereon, it is unlikely to provide an accurate representation of the efficacy of washing and cleaning of the washing apparatus.

It is therefore an aim of the present invention to provide washing test apparatus which removes the requirement for coating instruments with a test soil substance.

It is a further aim of the present invention to provide washing test apparatus which is quick and easy to use, thereby ensuring regular use of the apparatus.

It is a yet further aim of the present invention to provide washing test apparatus which provides a more accurate and multidirectional challenge that is representative of cleaning/washing efficacy in washing apparatus.

It is an aim of the present invention to provide holder means for use with a test soil device.

It is a further aim of the present invention to provide a test soil device for use with holder means.

According to a first aspect of the present invention there is provided washing test apparatus, said apparatus including holder means and one or more test soil devices for location with said holder means for allowing a washing process to be tested, said holder means including at least first and second members, characterised in that at least a portion of said first and/or second members is capable of undergoing relative movement to allow said one or more test soil devices to be located therebetween.

In one embodiment the at least first and second members are provided a pre-determined small distance apart and the test soil device is located between the members in use. A portion of the test soil device typically protrudes from the members when in position therebetween to allow the device to easily removed as required.

Preferably said at least first and second members are pivotally movable relative to each other. For example, the first and second members can be joined together via a hinge or pivot point.

The first and second members are movable between a first closed position, wherein the members are parallel with and substantially adjacent to each other, and a second open position, wherein at least a part of the members are spaced apart from each other sufficiently to allow a test device to be inserted therebetween or removed therefrom. The test device is located between the members when in the closed position in use and the members are arranged such that the test device cannot fall out from between the members in said closed position.

In one embodiment the first and second members include a handle portion and a test soil device holding portion. The test soil device holding portion is typically moved between said open and closed positions. The handle portion is typically gripped by a user to allow a user to move the test soil device holding portion between said open and closed positions.

Preferably the test soil device holding portion of one or more of said first and/or second members includes two or more surfaces which allow the attachment of one or more test soil devices thereto. The two or more surfaces are typically located at different angles or are orientated in different directions, thereby providing multi-directional washing test apparatus. In addition, these different angled surfaces help to secure the test soil device between the first and second members.

Alternatively the test soil device holding portions are substantially linear or straight in form.

In one embodiment the two or more surfaces include opposing surfaces of the test soil device holding portion (i.e. surfaces of the first and second members).

In a further embodiment the two or more surfaces include surfaces provided at an angle relative to each other on the first and/or second member. For example, in one example, the two or more surfaces are provided substantially perpendicular to each other on each member.

Preferably at least the test soil holding portion, the surfaces to which the test soil device is attached or between which the test soil device is attached are provided with one or more apertures therein to increase the exposure of the test soil device to washing fluid in the washing apparatus.

In one embodiment the apertures are provided in a grid like arrangement.

In a further embodiment the apertures are in the form of a mesh.

In either embodiment the provision of the aperture and walls of the holder means defining the apertures provides an open surface and a restricted surface for testing the efficacy of the washing process. This provides a good representation of a typical item of surgical or medical equipment, particularly hinged instruments such as scissors or forceps which are notoriously difficult to clean due to contaminants becoming trapped within the joints of the said instruments.

Preferably the first and second members are resiliently biased to said closed position. The biasing force is sufficient to secure, at least in part, the test soil device between the members in said closed position.

Further preferably the handle portion of the members is resiliently biased to said closed position. In this position, the handle portions of the members are a spaced distance apart and the test soil holding portions are parallel and adjacent each other.

A spring, sprung metal/plastic or other biasing means can be provided to bias the members/handle portion to said closed position.

The biasing means can also be the means by which the first and second members are attached together.

In one embodiment the holder means and/or the test soil holding portion is any or any combination of substantially round, substantially cylindrical, substantially semi-circular and/or any other required shape.

The first and second members and/or the test soil device holding portions can taper if required.

In the embodiment wherein the holder means is cylindrical, the first and second member are also substantially cylindrical and the first outer member is of slightly larger dimensions than said second inner member. As such, the second member can be located in the channel defined by the cylindrical walls of said first member. The test soil device is located between the first and second members and one or more apertures can be provided in the walls of the first and second members if required.

Preferably the one or more test soil devices are in the form of sheet material with a test soil substance provided thereon.

Preferably the test soil substance or indicator provided on the test soil device is printed onto a surface of sheet material and further preferably the test soil substance or indicator is printed onto both surfaces of the sheet material.

In providing the test soil substance on sheet material rather than coating instruments or medical devices, the test soil is easier and safer to handle. The test soil device is typically pre-prepared, thereby reducing the time required for a user to set up the test in washing apparatus. In addition, since the test soil device is detachably attached to the holder it can be easily removed for inspection and is maintained in a required orientation in the washing apparatus in use.

Preferably the sheet material is substantially flexible, thereby allowing the test soil device to be bent around angled first and/or second members, rolled up and located in channels or lumens of medical or surgical instruments to ensure adequate cleaning of the same.

Preferably the sheet material is formed from a plastic material, such as polypropylene.

The test soil substance or indicator does not include blood or blood related products but can contain any or any combination of proteins (typically from at least two sources), lipids and/or polysacharrides. Each of the components of the indicator present a unique challenge to the cleaning/washing process. For example, proteins require a cool wash below 35 degrees Celsius, whereas lipids require a higher temperature, preferably in the presence of a surfactant.

The indicator is provided in such a colour, by dye or other means to provide a clear visual indication as to the presence of contaminants thereon. If any residue is visible on the test device after washing, the test indicates that the washing/cleaning process has failed to provide an adequate cleaning/washing process. If no residue is visible on the test device after washing, the test indicates that the washing process meets the required criteria for cleaning/washing. The sheet material can be transparent or opaque to allow easy visualisation of the indicator thereon.

The degree to which the components of the indicator are adhered to the surface of the sheet material can be varied as required, thereby reflecting the ability to remove normal contaminants which have been dried onto instruments for different periods of time.

According to a second independent aspect of the present invention there is provided a test soil device for use with holder means.

The test soil device can be used independently of the holder means if required.

According to a further independent aspect of the present invention there is provided holder means for use with a test soil device.

Thus, it can be seen that the advantages of the present invention are that the test soil device is easier and safer to handle. In addition, it is quick and easy to visually inspect the device after the washing and cleaning processes to ensure that the processes have been successful. The holder means allows the test soil device to be easily located and maintained in different positions and at different angles in washing apparatus to provide a more accurate representation of washing conditions throughout the apparatus.

An embodiment of the present invention will now be described with reference to the accompanying figures, wherein:

FIGS. 9a-9d illustrate views of an inner member for attachment with the outer member shown in FIG. 8a;

Referring to the figures, there is illustrated washing test apparatus 2 including a holder 4 and a test soil device 6.

Holder 4 includes first and second members 8, 10 pivotally connected to each other at pivot point 12. First and second members 8, 10 each have a handle portion 14, 16 and a test soil device holding portion 18, 20.

Figure 1A:
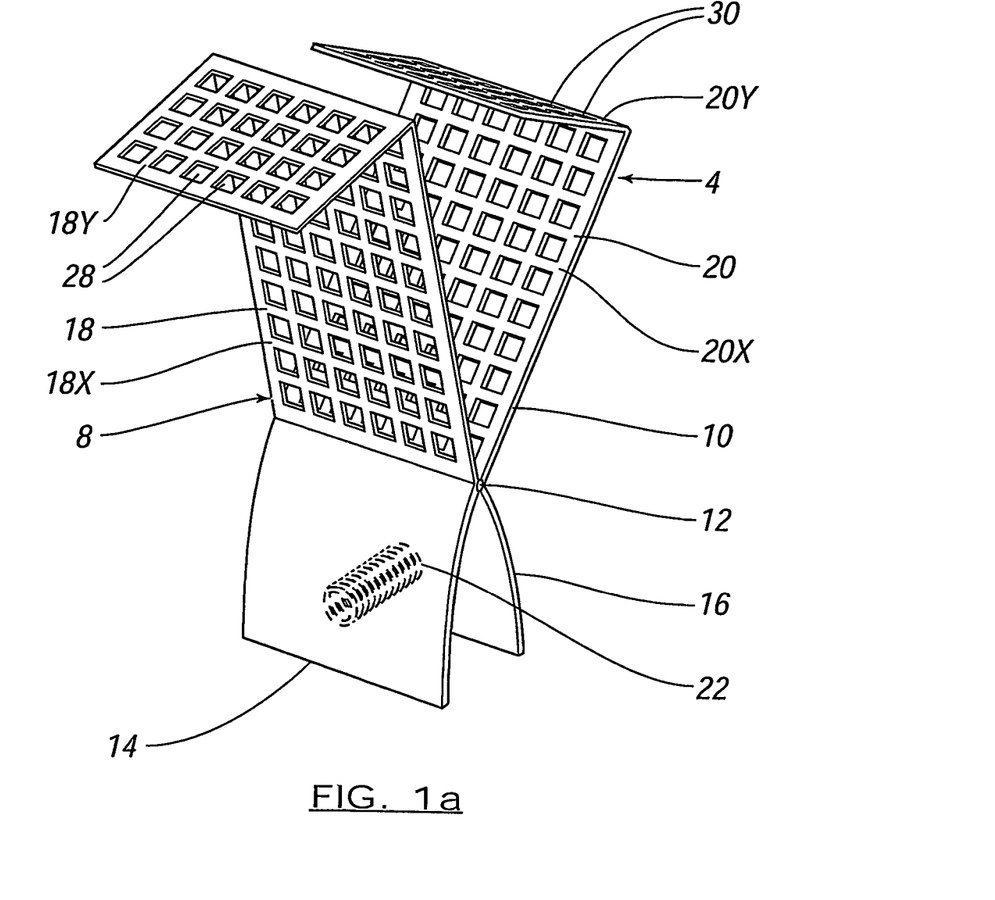
FIGS. 1a and 1b are perspective views of holder means according to an embodiment of the present invention in open and closed positions.
Figure 1B:
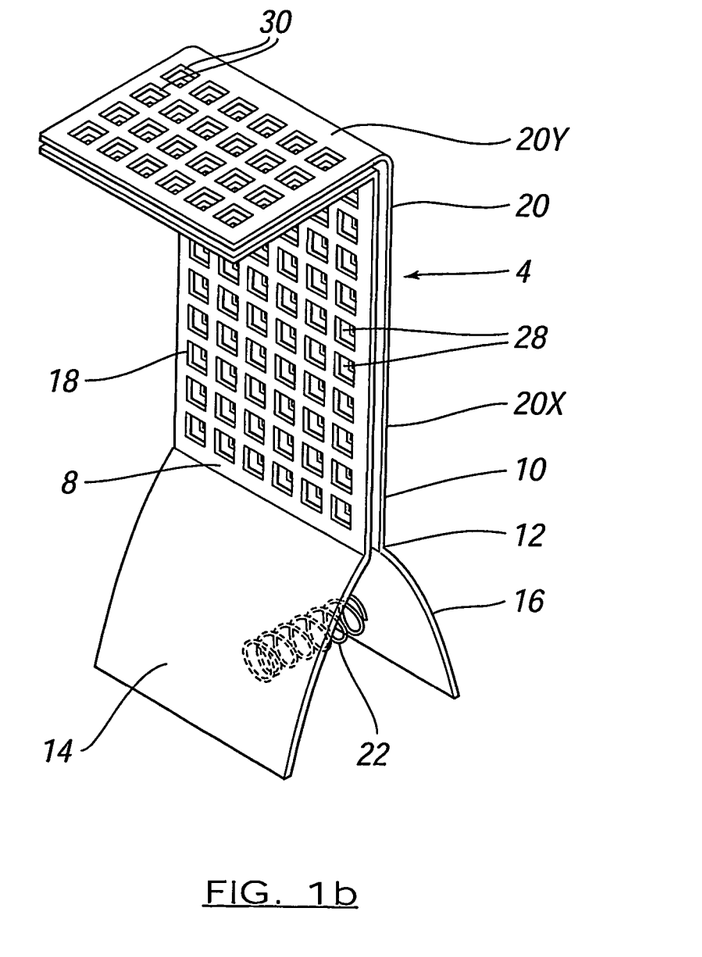

A spring 22 is attached to opposing surfaces 24, 26 of handle portions 14, 16 which biases the handle portions to a closed position, as shown in FIG. 1b. In this position, the handle portions are a spaced distance apart and the holding portions 18, 20 are adjacent and parallel to each other.

First and second members 8, 10 are movable between the closed position, shown in FIG. 1b, to an open position, shown in FIG. 1a, by gripping handle portions 14, 16 and moving the same towards each other, thereby compressing spring 22 and causing holding portions 18, 20 to move apart about pivot point 12.

Holding portions 18, 20 include sub-portions 18X, 18Y and 20X, 20Y, the sub portions within each holding portion being substantially perpendicular to each other. Sub-portions 18X and 20X are substantially parallel and adjacent each other in said closed position and sub-portions 20S and 20Y are substantially parallel and adjacent each other in said closed position. The provision of the sub-portions at different angles increases the ease with which the holder can be located in a required position during a washing process and also provides multi-directional wash testing.

Each of said sub-portions 18X, 18Y, 20X, 20Y is provided with a plurality of apertures 28, 30 arranged in a grid format. When first and second members 8, 10 are in a closed position, such that the members are parallel to and in contact or are at least adjacent to each other, the apertures 28 on the first members are substantially aligned with apertures 30 on said second member. However, the apertures 28, 30 can be provided out of alignment if required.

Figure 3:
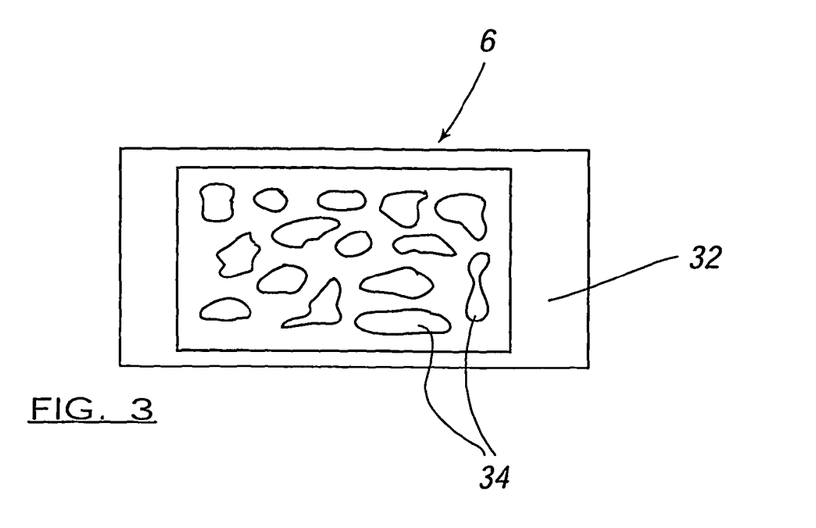
FIG. 3 illustrates a test soil device used in the apparatus in FIG. 2b.

Test soil device 6 includes sheet material having an upper surface 32 and a lower surface (not shown). An indicator 34 is provided on both the upper and lower surfaces in a predetermined pattern by a printing process and allowed to dry onto the sheet material. The indicator 34 is provided in a contrasting colour to the colour of the sheet material, thereby allowing easy visualisation of the indicator.

The indicator typically includes lipids, polysacharrides and at least two proteins and represents typical substances located on medical or surgical instruments after use in clinical or laboratory procedures.

Figure 2A:
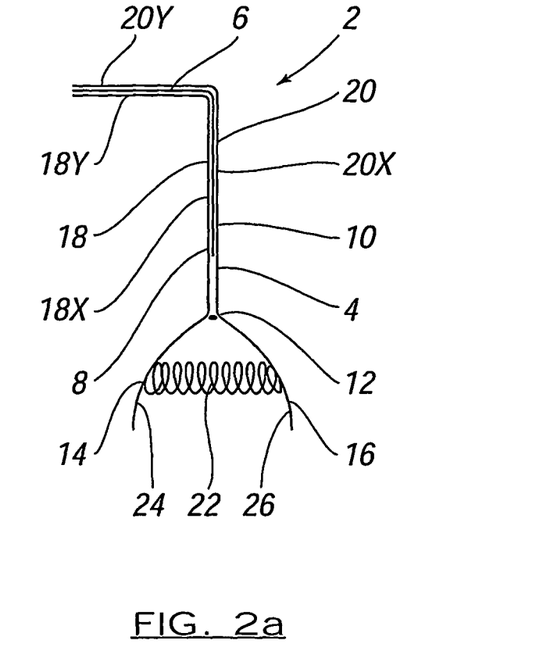
FIGS. 2a and 2b illustrate side views of the holder means and test soil device in open and closed positions respectively.
Figure 2B:
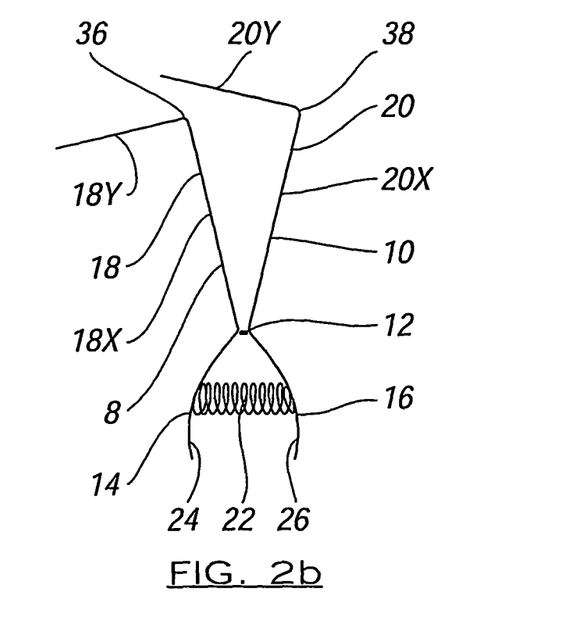
Figure 2C:
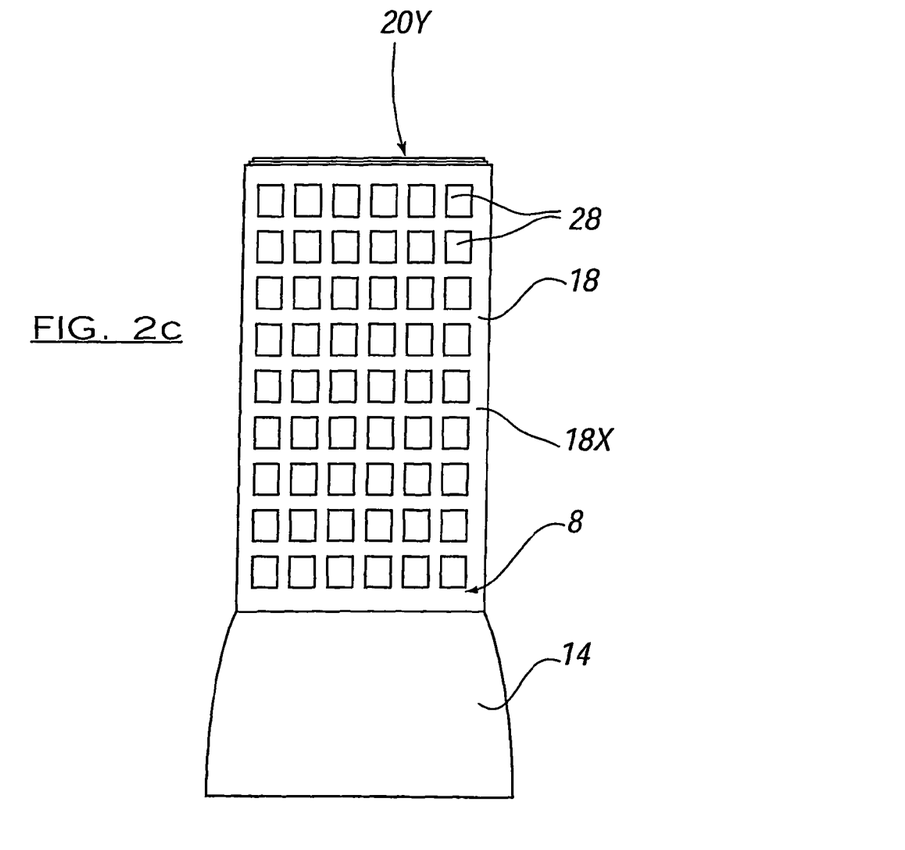
FIG. 2c is a front view of the holder means in FIGS. 1a-2b.

In use of the wash test apparatus, the holding portions 18, 20 of holder 4 are moved to an open position by applying a compressive force to handle portions 14, 16. Soil test device 6 is inserted between holding portions 18, 20 and holder 4 is closed by removing the compressive form on the handle portions, thereby biasing the handle portions and thus the holding portions 18, 20 to a closed position. Device 6 is slightly smaller in length than the combined lengths of sub portions 18X and 18Y or 20X, 20Y. As such, when holder 4 is moved to a closed position, device 6 is folded adjacent the edge 36, 38 defining sub portions 18X, 18Y and 20X, 20Y and follows the contours (which in this example are substantially planar) of the sub-portions 18X, 18Y, 20X, 20Y, as shown in FIG. 2b. It is to be noted that a number of separate test soil devices can be provided and positioned adjacent sub-portions 18X, 18Y, 20X, 20Y if required.

The indicator 34 is typically provided in a substantially central portion of the sheet material such that a border is formed around the periphery of device 6. This border corresponds to the peripheral edge of holding portions 18, 20 which are not provided with apertures 28, 30.

With the soil test device 6 located between the holding portions 18, 20 of holder 4, portions of indicator 34 on both sides of the sheet material are accessible to water and other washing detergents or substances via apertures 28, 30. In particular, four surfaces 18Y, 20Y, 18X and 18Y facing different directions and positioned at different orientations are presented for washing in this example, thereby providing a more accurate indication as to the efficacy of the washing process than conventional unidirectional devices.

The holder can be located at any required position in the washing apparatus as required. The provision of different angled surfaces allows the holder to be positioned and balanced in a required position with greater ease than conventional devices.

The holder is typically made from stainless steel, in order to simulate the typical specific heat capacity of surgical instruments and other medical devices, and also to reduce the risk of damage to the same as a result of use of extreme washing conditions or detergents.

Once the washing process has taken place, a user can quickly and easily remove the soil test device from the holder 4 by moving the holder to an open position. If the washing/cleaning process has been successful, the indicator 34 will be absent from the device. If the washing/cleaning process has been unsuccessful, the indicator will still be present on the device.

Figure 7A:
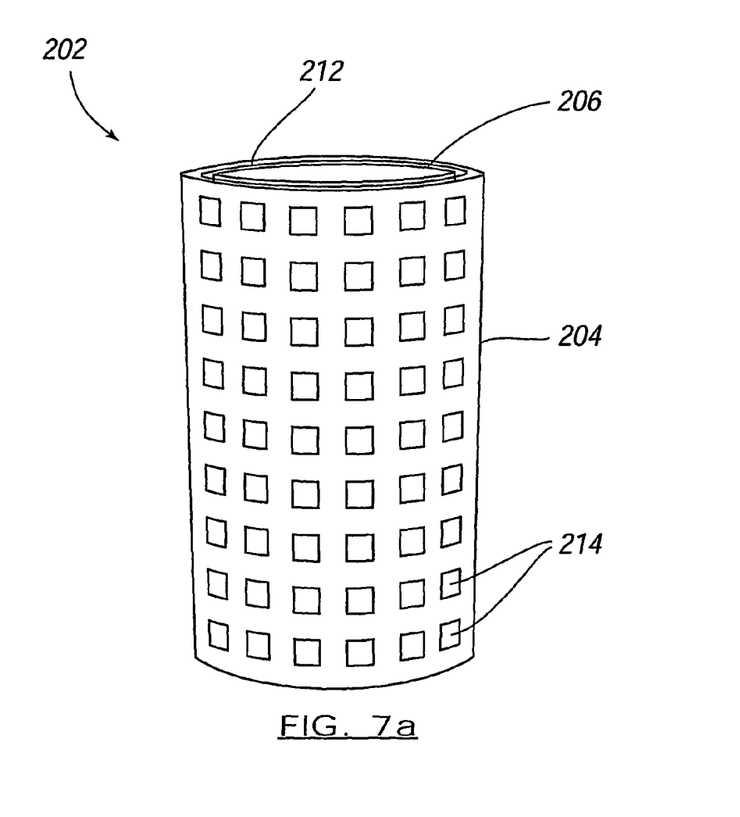
FIGS. 7a-7d illustrate further examples of holder means according to the present invention.
Figure 7B:
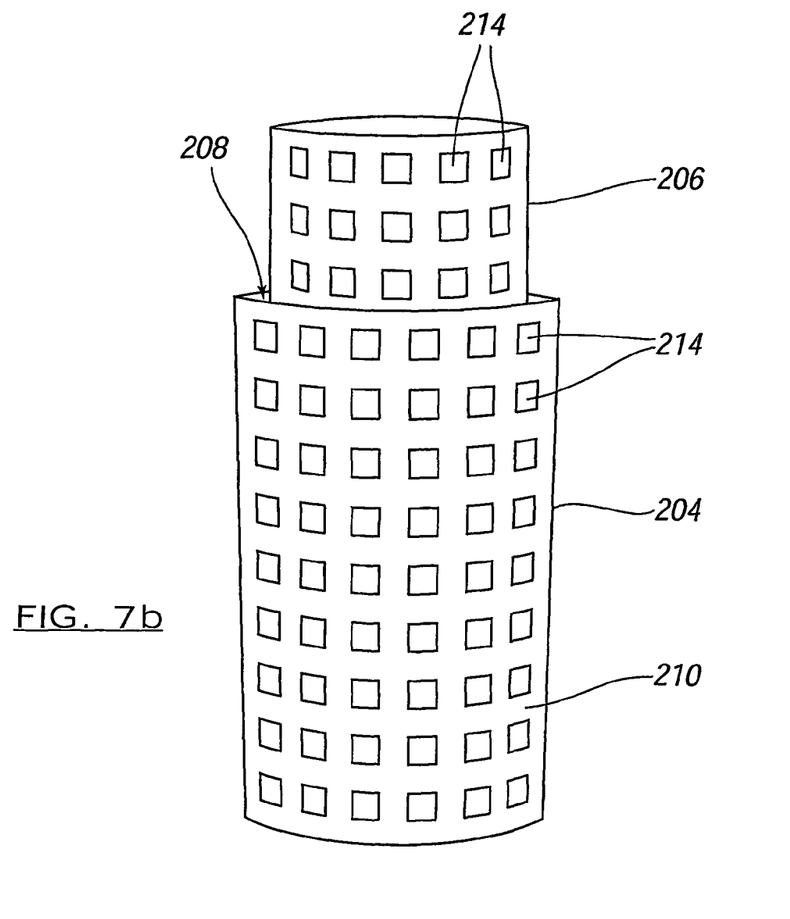

Further examples of holder means according to the present invention are illustrated in FIGS. 7a-7d. In FIGS. 7a and 7b, a substantially cylindrical holder means 202 is provided and includes a first outer cylindrical member 204 and a second inner cylindrical member 206. Second member 206 is slidably located in the channel 208 defined by walls 210 of first member 204 between a first position, wherein member 206 is substantially encased by first member 204, as shown in FIG. 7a, and a second position, wherein member 206 is removed in whole or part from channel 208 of first member 204 (FIG. 7b illustrates member 206 partially removed from first member 204). Test soil device 212 is located and secured between the first and second members 204, 206 when in the first position, as shown in FIG. 7a. Apertures 214 can be provided on both the inner and outer members 204, 206 as required. The holder means according to this embodiment allows the washing efficiency to be tested over its 360 degree perimeter. The first and second members can also be tapered if required. The holder means shown can include a handle or gripping portion if required, although one is not shown for the purposes of clarity.

Figure 7C:
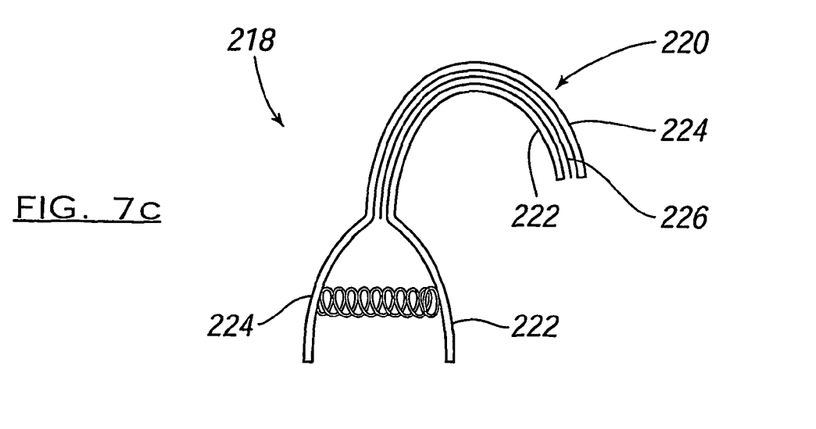
Figure 7D:
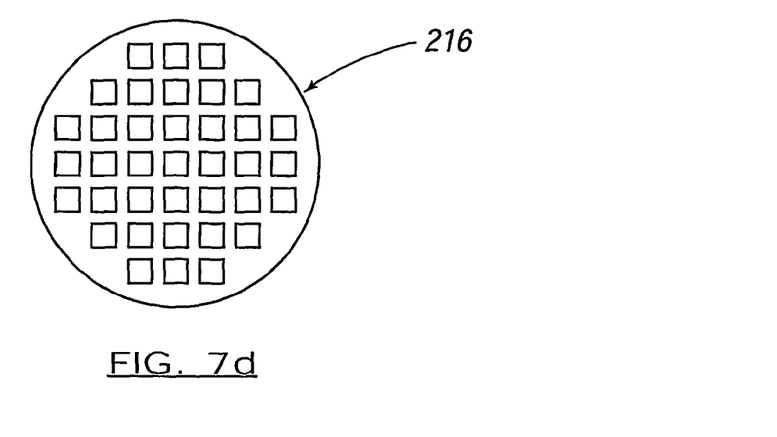
Figure 8A:
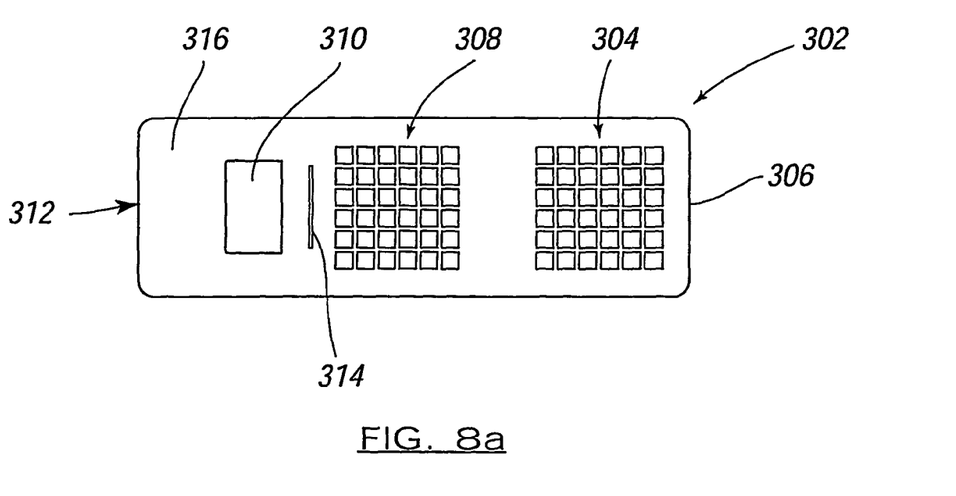
FIG. 8a illustrates a blank of an outer member forming the holder means in one embodiment.
Figure 8B:
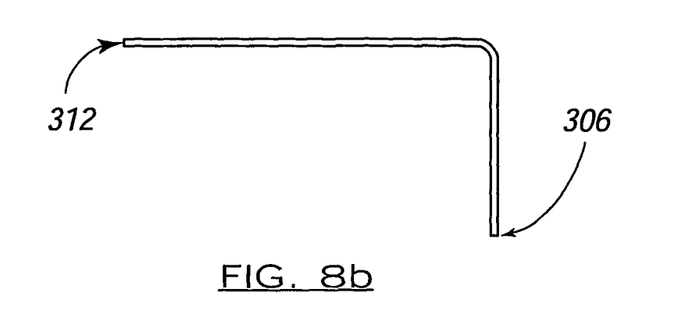
FIGS. 8b-8e illustrates a side view, front view, end view and perspective view of the member in FIG. 8a when formed.
Figure 8C:
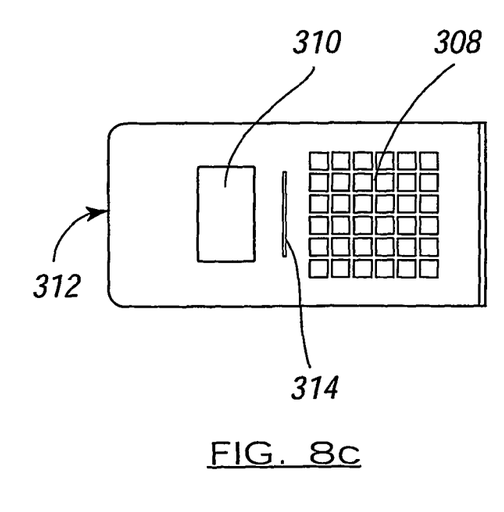
Figure 8D:
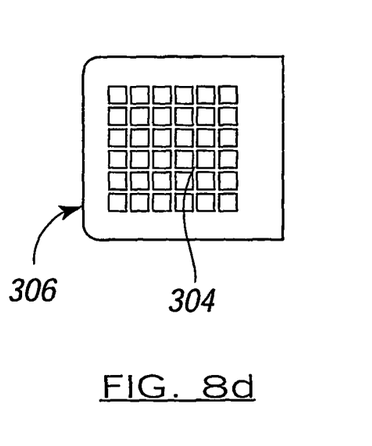
Figure 8E:
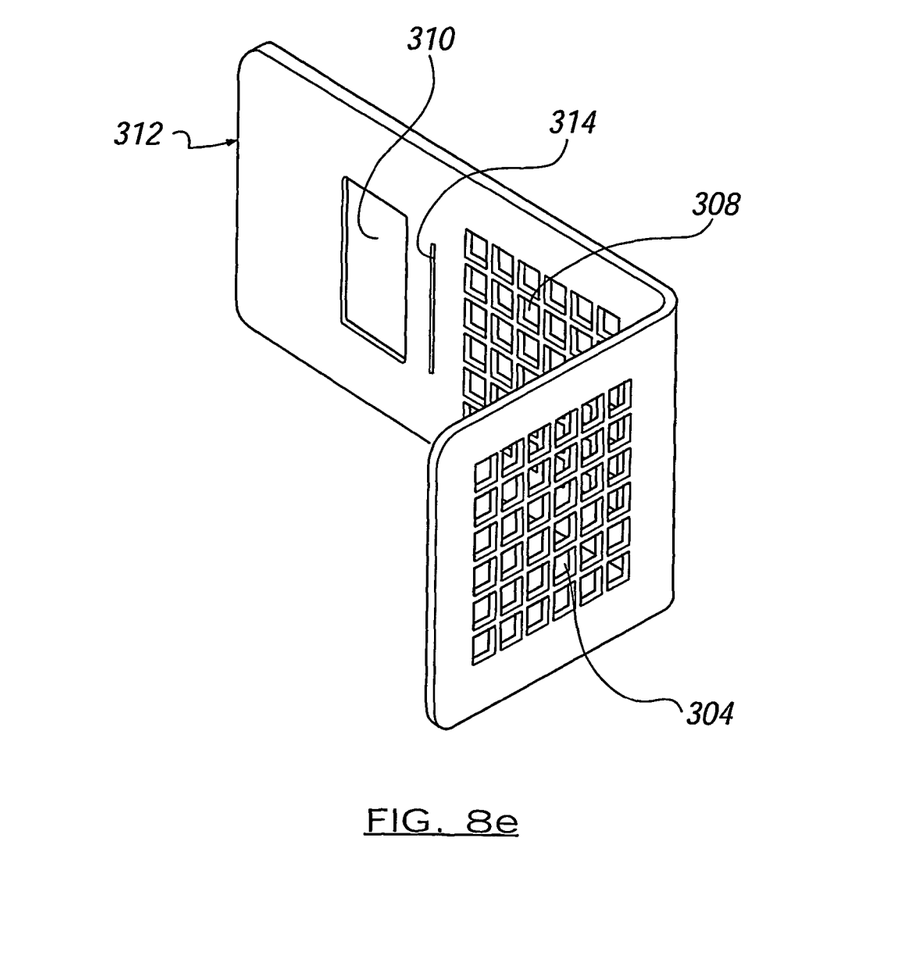
Figures 9A, 9B:
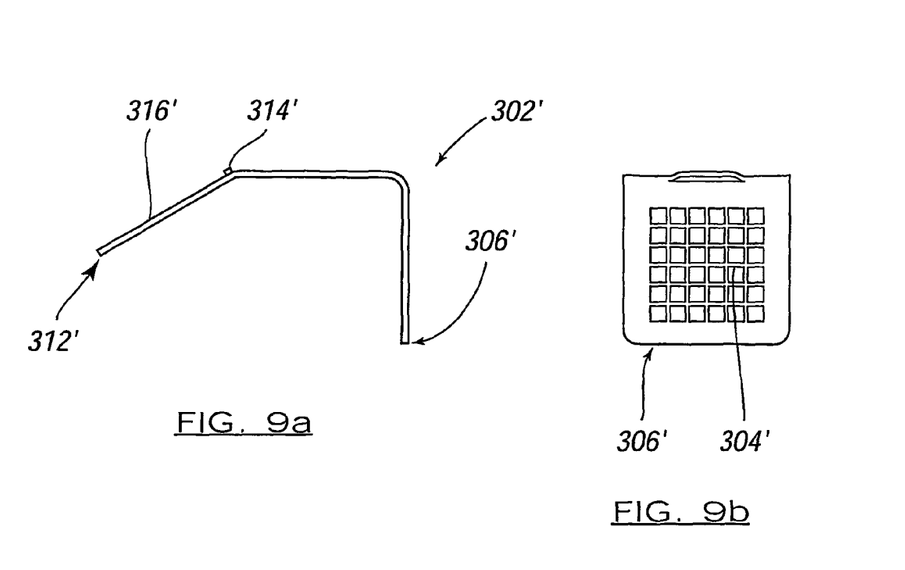
Figure 9C:
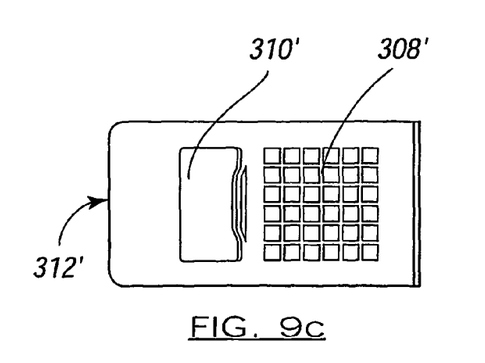
Figure 9D:
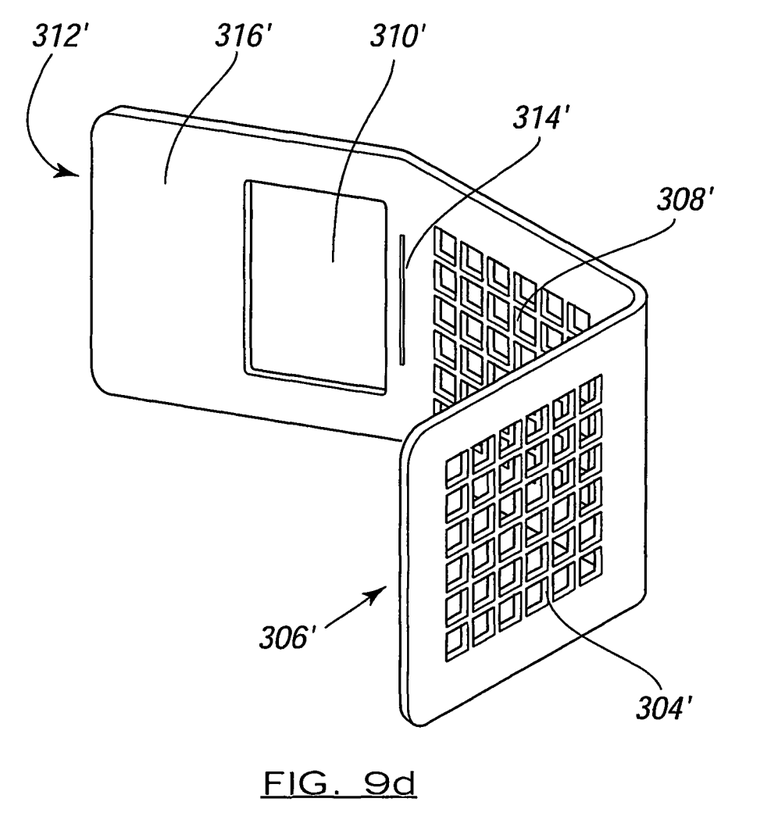
Figure 9E:
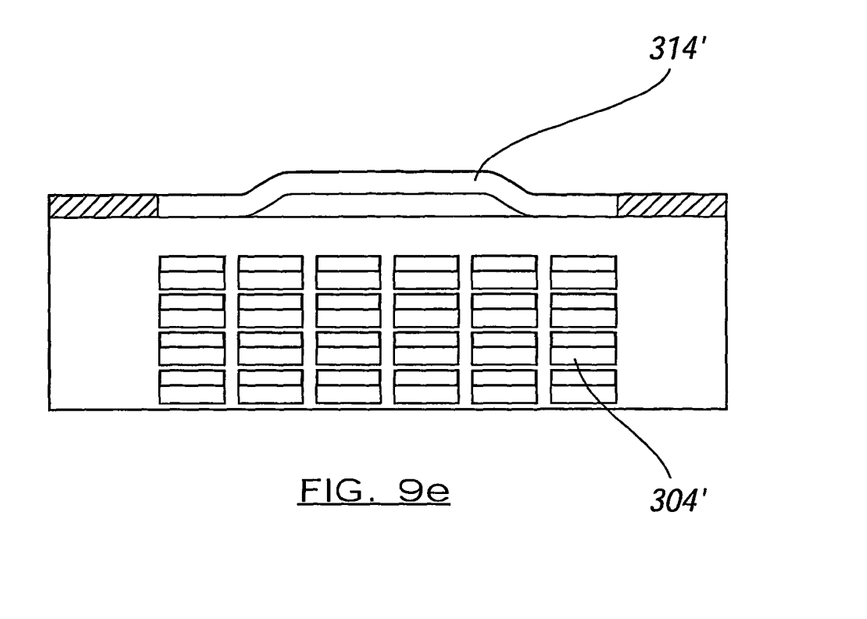
FIG. 9e is an enlarged view of the top edge of the member shown in FIG. 9c.

FIG. 7*d*, illustrates a hollow spherical holder means 216 wherein the washing efficiency in substantially all directions can be tested. In this example, first and second member can be hemispherical in shape and hinged or detachably attached along at least an arc of the outer surface thereof, the test soil device typically being located in the sphere 216. Alternatively, the first member can be in the form of an outer sphere and the second member can be in the form of an inner sphere located in the outer sphere in use. The first member typically has means for separating portions of the sphere to allow the second member to be located therein. The test soil device in this example is typically located between the outer and inner spheres.

Referring to FIG. 7*c*, a holder means 218 is provided wherein the test soil device holding portion 220 of the first and second members 222, 224 is substantially semicircular in shape. The test soil device 226 is located between the first and second members in the normal manner.

Figure 4:
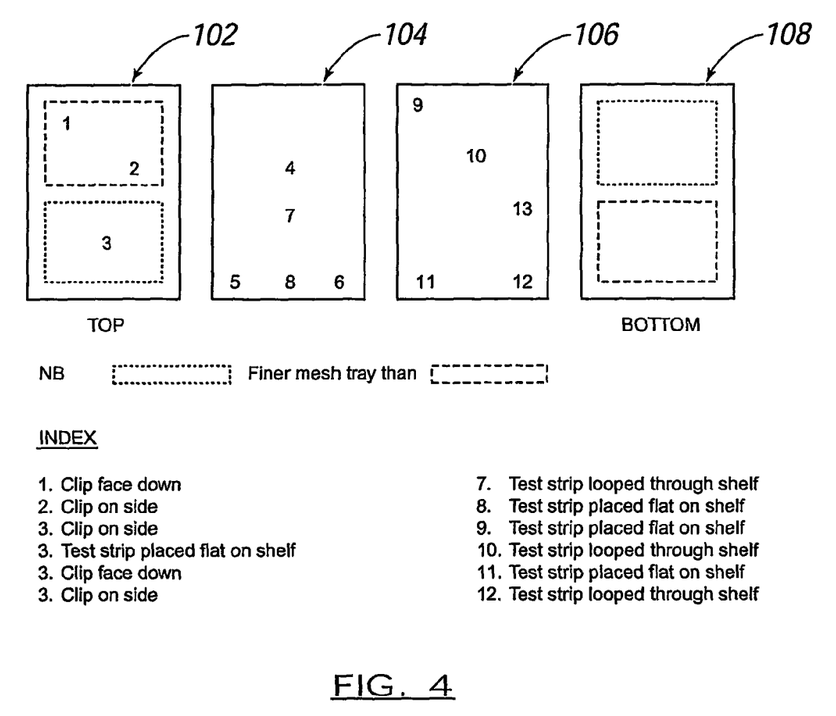
FIGS. 4-6 illustrate the locations of washing test apparatus in washing apparatus in three different examples.

An example of use of the washing test apparatus in a washing process will now be described with reference to FIG. 4. The washing apparatus is in the form of a washer disinfector consisting of four shelves 102, 104, 106, 108, each shelf having a spray arm for spraying cleaning fluid into the apparatus.

The washing cycle used in the first example includes the following steps:
Pre-rinse with cold water for 2 minutes
Drain
Main Wash at 60° C. for 3 minutes
Drain
Rinse for 1 minute with warm water
Drain
Rinse for 1 minute with warm water
Drain A plurality of test soil devices are located in holders and loose on the four shelves throughout the washing apparatus. Test soil devices in holders/clips are provided with reference numerals 1-3, 5-6 and test soil devices located directly onto the shelves in the washing apparatus are provided with reference numerals 4, 7-12. It was found that the indicators of all test soil devices were washed off except those of test soil devices 2, 5 and 6. Sample 12 also had indicator left thereon in the region where the test soil device was stapled together. As such, this provides a clear indication to a user that certain regions of the washing apparatus provide a greater washing/cleaning efficacy than other regions. This is important to know so that surgical and medical instruments in all regions of the washing apparatus are adequately washed or cleaned.

Figure 5:
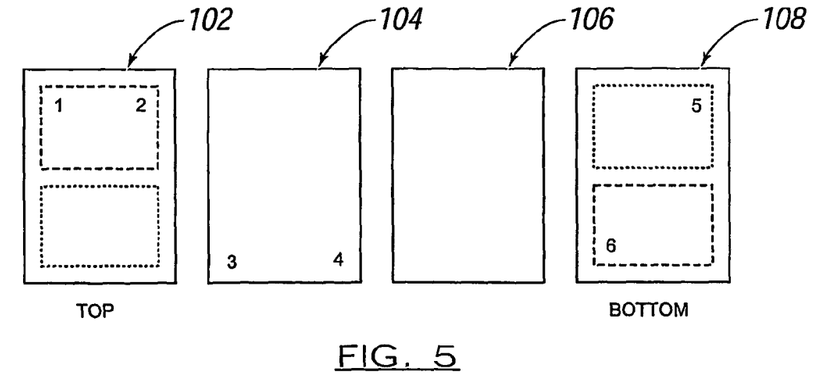

In a second example, the washing process was repeated but a detergent was added in the main wash at 40° C. at a dosage of 5-10 ml per Liter. The washing apparatus typically holds 15 liters of water and thus 100 ml of detergent was used in the process. All soil test devices were located in holders and positioned in the washing apparatus on their sides according to FIG. 5 so that the mesh or apertures of the holder faced the chamber wall of the washing apparatus. It is generally acknowledged that areas of the load facing the chamber walls may be more difficult to clean than areas of the load directly facing spray arms or jets.

It was found that samples 2, 3 and 4 all had indicator residue clearly visible after the washing process and samples 5 and 6 had small quantities of indicator residue remaining. Sample 1 had no indicator residue remaining. These results were in line with expectations of the cleaning performance in this particular machine.

In a third example, the washing process was repeated with the following steps:

Pre-rinse with hot water at 60° C. for 2 minutes
Drain
Main Wash at 60° C. for 3 minutes
Drain
Rinse for 1 minute with warm water
Drain
Rinse for 1 minute with warm water
Drain Detergent was used in the washing process at the same dosage as in example 2 and at the same temperature. After the pre-wash at 60° C., the temperature of the water dropped to 30° C. due to lack of hot water and the water was then slowly increased for about 3.5 minutes to 60° C. before the main wash stage commenced.

Figure 6:
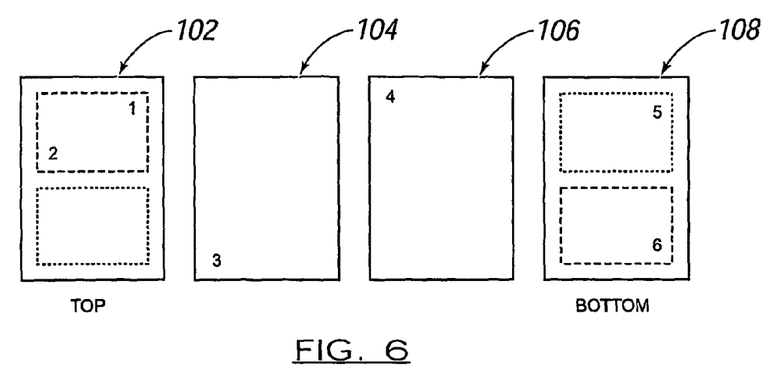

The soil test devices were once again all provided in the holders and were positioned facing the chamber walls of the washing apparatus in accordance with FIG. 6.

The results of this third washing process showed that all indicators were still present and visible on the test soil devices.

It can therefore be seen that the apparatus of the present invention can be used to provide a reliable test for the level and degree of washing taking place in the washing apparatus under different washing conditions and at different locations in the washing apparatus. This is extremely important since different contaminants require washing at different temperatures, such as proteins which, if not washed at a temperature below 35° C., become denatured and become extremely difficult to remove.

Referring to FIGS. 8*a*-8*e*, there is illustrated a blank 302 of a member in one embodiment of the present invention. The blank 302 includes a first arrangement of apertures 304 arranged in a grid format adjacent end 306 and a second arrangement of apertures 308 arranged in a grid format. A border is provided around each arrangement of apertures. Apertures 308 are provided a spaced distance apart from apertures 304 and an aperture 310 provided at end 312. The blank can be formed into a required shape according to any conventional method, such as bending and/or the like. The apertures are typically cut by nitrogen laser cutting but other conventional techniques can also be employed.

Figure 10:
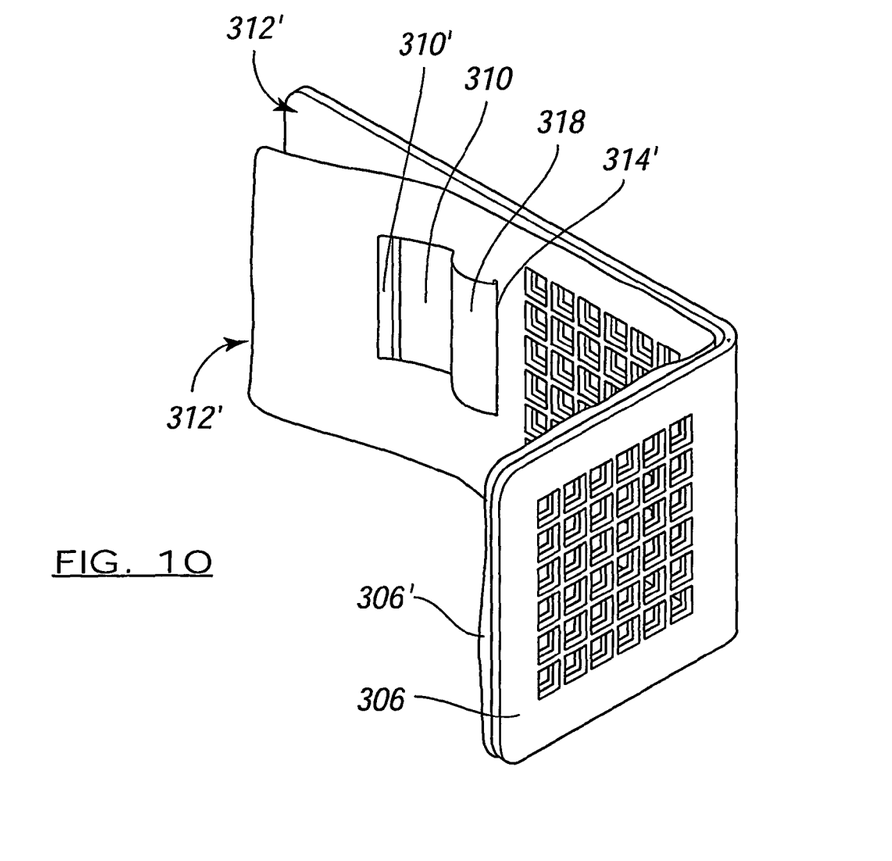
FIG. 10 is a perspective view of the members in FIGS. 8 and 9 joined together in a closed position.

FIGS. 8*b*-8*e* illustrate the member when formed and end 306 is bent so that apertures 304 are substantially perpendicular to apertures 308. A further substantially identical member 302' (FIGS. 9*a*-9*e*, the same features are identified by a ') can then be attached to member 302 by means of an attachment, such as a portion of sprung metal or a metal clip 318 as shown in FIG. 10, which is typically attached to one of the members and located through aperture 310 and 310' on the other of said members. This clip or portion can also act as biasing means if required. A slot or recess 314 can be provided to allow the attachment of one end of the sprung metal or clip therein. Member 302 typically forms the outer member and member 302' typically forms the inner member when said members are joined together.

FIGS. 9*a*-9*e* illustrate various views of the further member 302' formed according to a different arrangement to that illustrated in FIGS. 8*a*-8*e*. In this arrangement, end 312' has been bent relative to the surface of member 302' on which apertures 308' are provided, in addition to bending of end 306' to form a handle portion. In the final arrangement, end 312' faces inwardly of the member towards end 306'. A pivot point or fulcrum 314' is provided in the form of a bridge or protruding portion to allow member 302' to pivot with respect to member 302.

Members 302 and 302' are arranged in a substantially overlapping arrangement when joined together in a first closed position, and apertures 304, 308 are substantially aligned and adjacent each other. Portion 316' is a spaced distance apart from portion 316, thereby allowing portion 316' to be gripped by a user in use and moved towards portion 316. The clip 318 joining members 302 and 302' together allows member 302' to pivot away from member 302, thereby allowing a test soil device to be located therebetween and/or removed.

The holder of the present invention can be provided in any required shape, size and/or design and can present a variety of surfaces which differ in number, direction or orientation as required, thereby providing a more stringent test for decontamination processes than prior art devices. The test soil devices of the present invention can be used alone if required to provide an indication as to the spray and jet patterns within the washing apparatus. The test soil devices can also be suspended in ultrasonic cleaners to allow identification of low ultrasonic activity. Furthermore the flexibility of the sheet material from which the test soil devices are formed allows the same to be rolled into a substantially cylindrical shape for location in tubes or to reflect the degree of washing in tubes and other lumen or channel containing instruments. The advantage of rolling the indicator sheet material into a tube is that the indicator sheet material may be subsequently unrolled after the process. This allows visual examination of the internal surfaces of a narrow bore or lumen, which would not normally be possible by conventional means.

The invention claimed is:

1. A washing test apparatus comprising:
   a sheet of material comprising an indicator, the indicator comprising a colorant, a protein, a lipid, and a polysaccharide; and
   a holding device comprising at least first and second members joined together by a hinge, at least a portion of said first and/or second members being capable of undergoing relative movement between an open position and a closed position to allow for removable insertion of said sheet therebetween, and a spring positioned between the first and second members to bias said portion of said first and/or second members toward the closed position, wherein said sheet is removably retained between said portion of the first and/or second members while in the closed position, and said portion includes two or more surfaces provided in different directions, angles and/or orientations relative to each other, said sheet following the contours of said surfaces when located therebetween to allow multi-directional wash testing and to maintain said sheet in position during use.

2. The apparatus according to claim 1 wherein while said portion of said first and/or second members is in the closed position, the first and second members are substantially parallel and adjacent each other.

3. The apparatus according to claim 1 wherein the first and/or second members further comprise a handle portion.

4. The apparatus according to claim 1, wherein one of said first and second members includes said two or more surfaces.

5. The apparatus according to claim 1, wherein the two or more surfaces include opposing surfaces of the first and second members.

6. The apparatus according to claim 1, wherein each of said first and second members is provided with a first surface and a second surface substantially perpendicular thereto.

7. The apparatus according to claim 1, wherein said portion of said first and/or second members that removably retains said sheet is provided with one or more apertures therein.

8. The apparatus according to claim 7, wherein the apertures of said first and second members are substantially aligned.

9. The apparatus according to claim 7, wherein the apertures are provided in a grid like arrangement.

10. The apparatus according to claim 7, wherein the apertures are in the form of a mesh.

11. The apparatus according to claim 1, wherein the first and second members further comprise a handle portion and the spring is positioned between the handle portion of the first and second members to resiliently bias the first and second members to said closed position.

12. The apparatus according to claim 1, wherein the spring attaches the first and second members together.

13. The apparatus according to claim 1, wherein said portion that removably retains the sheet is substantially round, substantially cylindrical, substantially semi-circular, or any combination thereof.

14. The apparatus according to claim 1, wherein said portion that removably retains the sheet is tapered.

15. The apparatus according to claim 1, wherein the first and/or second members are substantially round, substantially semi-circular, or any combination thereof.

16. The apparatus according to claim 1, wherein the indicator is printed onto a surface of the sheet.

17. The apparatus according to claim 1, wherein the sheet of material is formed from a plastic material.

18. The apparatus according to claim 1, wherein the sheet of material is substantially transparent.

19. The apparatus according to claim 1, wherein the sheet of material is opaque.

20. The apparatus according to claim 1, wherein a portion of the sheet of material protrudes from the first and/or second members when in position therebetween in use.

21. The apparatus according to claim 1, wherein both of said first and second members include said two or more surfaces.

* * * * *